United States Patent [19]

Chen et al.

[11] Patent Number: 4,504,364

[45] Date of Patent: Mar. 12, 1985

[54] PHENOL PURIFICATION

[75] Inventors: Jamin Chen, Montville; Ali M. Khonsari, Bloomfield; George D. Suciu, Ridgewood, all of N.J.

[73] Assignee: The Lummus Company, Bloomfield, N.J.

[21] Appl. No.: 392,568

[22] Filed: Jun. 28, 1982

[51] Int. Cl.³ .............................................. C07C 37/76
[52] U.S. Cl. ........................................ 203/45; 203/46; 203/83; 203/96; 203/98; 568/754
[58] Field of Search ..................... 203/43–46, 203/98, 181, 69, 83, 96, 95, 92; 568/754

[56] References Cited

U.S. PATENT DOCUMENTS

| 2,486,342 | 10/1949 | Taylor et al. | 203/18 |
| 3,692,845 | 9/1972 | Cheema et al. | 568/754 |
| 3,810,946 | 5/1974 | Yeh et al. | 568/754 |
| 4,298,765 | 11/1981 | Cochran et al. | 568/754 |
| 4,351,967 | 9/1982 | Nishimura et al. | 568/754 |

Primary Examiner—Wilbur Bascomb
Attorney, Agent, or Firm—Elliot M. Olstein

[57] ABSTRACT

In the production of high purity phenol, a water-phenol mixture recovered from the top of a distillation column is contacted with a water immiscible solvent to extract methyl benzofuran and other by-products and impurities in phenol production therefrom, with the extraction being accomplished at a temperature at which the water-phenol mixture is present as a single phase liquid. The remaining mixture of phenol and water is recycled to the distillation.

11 Claims, 1 Drawing Figure

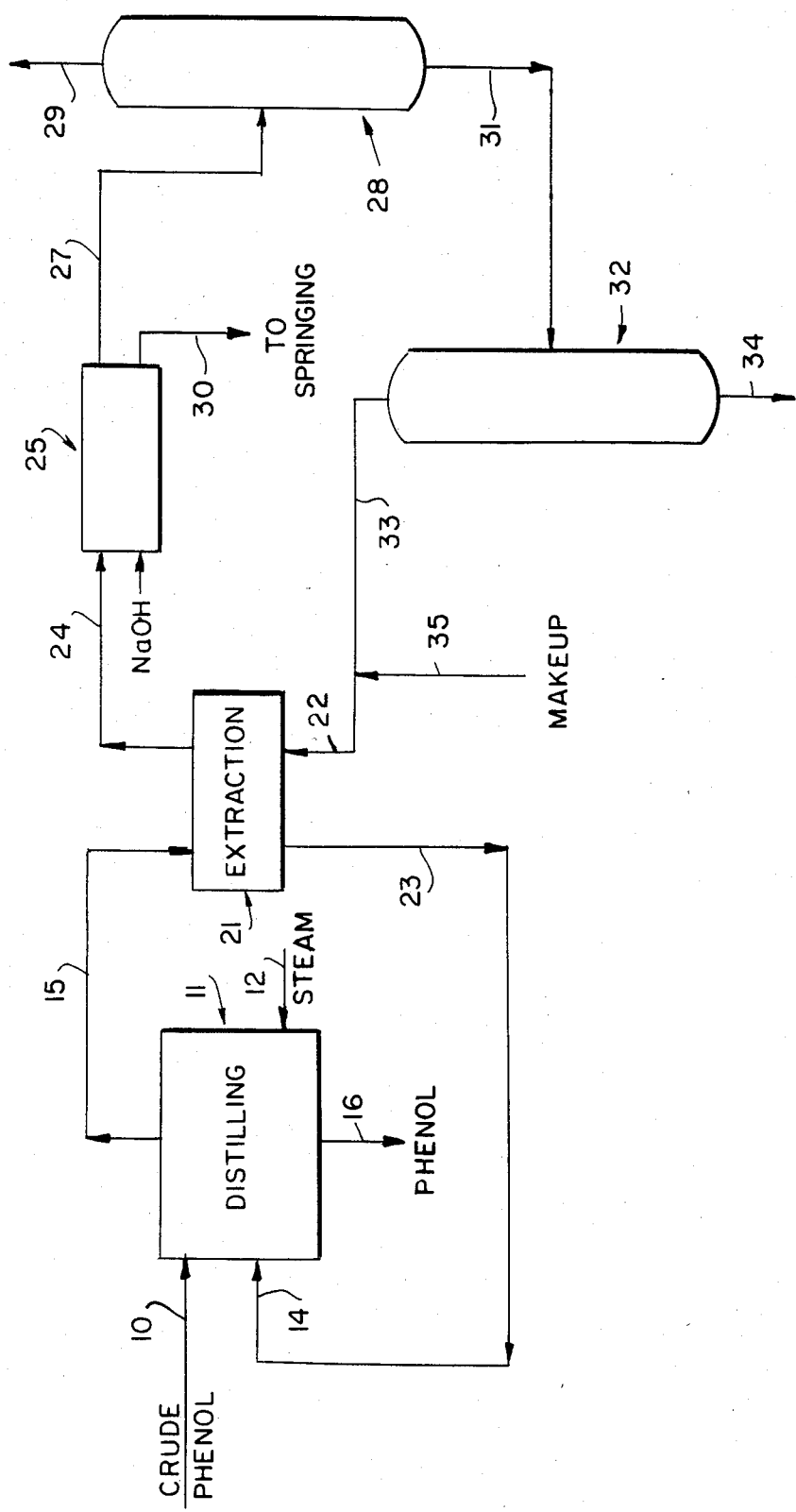

PHENOL PURIFICATION

This invention relates to the production of phenol, and more particularly to the production of high purity phenol.

In the production of high purity phenol, crude phenol obtained, for example, by the oxidation of cumene to cumene hydroperoxide, and acid cleavage of such hydroperoxide to phenol and acetone, followed by recovery of a crude phenol, is further purified to remove impurities such as acetol, mesityl oxide, acetophenone, 2- and 3-methyl benzofurans (collectively or individually methyl benzofuran or MBF), etc.

In one such process, the crude phenol is treated with an amine, followed by the addition of acid or acid anhydride and distillation to recover high purity phenol with such a procedure being disclosed in U.S. Pat. No. 3,692,845.

U.S. Pat. No. 4,298,765 describes an improvement in such a procedure wherein, after treatment with base, and optionally an acid or acid anhydride, the treated phenol is distilled in the presence of water to recover from the top of the column a phenol-water azeotrope which contains the majority of the MBF and other impurities, initially present in the treated phenol. Water present in the azeotrope is treated to separate MBF and the other impurities so as to enable recycle of such water to the distillation.

In accordance with the aforesaid patent, the water in the overhead is treated, after an initial separation from a phenol phase, with a solvent to extract organics therefrom, or the phenol-water mixture is treated with a solvent, followed by phase separation of organics. In such a process, a significant portion of the phenol present in the overhead is recovered in the organic phase, and it is then necessary to separately treat such organic phase to recover such significant portion of phenol. Such recovery increases overall costs.

In accordance with the present invention, there is provided a process for purifying phenol by distillation in the presence of water wherein the mixture of water and phenol recovered from the distillation overhead is contacted with a water immiscible solvent to extract MBF and other impurities, with the contacting being effected at a temperature at which the water-phenol mixture forms a single phase liquid. The solvent, containing extracted MBF and other impurities (extract), is separated from the remaining homogeneous liquid mixture of phenol and water (raffinate). The raffinate which contains the majority of the phenol originally present in the distillation overhead may be recycled to the distillation.

More particularly, by extracting MBF and other impurities, from a homogeneous liquid mixture of phenol and water, and by controlling the amount of extraction solvent, Applicants have found that it is possible to extract MBF and other impurities, while minimizing the amount of phenol extracted into the organic liquid phase forming the extract. In this manner, only a minimum of phenol must be recovered from the extract, thereby reducing overall costs.

The extraction is accomplished at a temperature at which the water and the phenol present in the mixture recovered from the top of the distillation column are completely miscible with each other so as to obtain a single phase liquid mixture. The exact temperature is dependent upon the relative portions of phenol and water in the mixture; however, water and phenol are miscible in all proportions at temperatures above 67° C. In general, the extraction is accomplished at a temperature in excess of 50° C., and such temperature is preferably at least 67° C. so as to insure complete miscibility of phenol and water.

The extraction solvent which is employed for extracting MBF and other impurities from the mixture is employed in an amount which is sufficient for such extraction, and which amount minimizes the amount of phenol extracted into the solvent. In general, the solvent is employed in an amount of no greater than 5 volume percent, and preferably no greater than 2 volume percent of the phenol-water mixture from which the MBF and other impurities is to be extracted. Of course, as should be apparent from the teachings herein, it is preferred to minimize the amount of extraction solvent employed consistent with achieving the desired extraction of MBF and other impurities from the phenol-water mixture. In most cases, the organic solvent is used in an amount of at least 0.1 and preferably at least 0.5 volume percent of the phenol-water mixture, and not in excess of 1 volume percent of the mixture.

The extraction solvent may be any one of a wide variety of organic solvents which are not miscible with water, and which is capable of extracting MBF and other impurities from the phenol-water mixture. In general, aromatic hydrocarbons are preferred, with such aromatic hydrocarbons most preferably being those which are indigenous to the process for manufacturing phenol, such as cumene, alpha-methyl styrene and the like. As representative examples of suitable solvents, there may be mentioned: aliphatic hydrocarbons (hexane, heptane, etc.), aromatic hydrocarbons (benzene and alkyl benzenes) chlorinated hydrocarbons (chloroform, carbon tetrachloride, etc.) esters (ethylacetate, etc.) and others. Mixtures of solvents can also be used. Preferred are solvents which have a good extraction capacity for MBF and the other impurities, have a low solubility in water and boil at temperatures higher than those used in the extraction.

After extraction, the phenol-water solution is recycled to the distillation. Appropriate amounts of make-up water are added to the recycle in order to compensate for the water which had dissolved in the organic phase (extract). The make-up water need not be pure. Any aqueous stream from the phenol plant can be used if it is similar in composition with the recycle stream.

The recycle stream need not be cooled. Actually, it is desirable to maintain its temperature higher than that at which an organic phase (predominantly phenol) separates out in order not to create inhomogeneities in its composition. If phase separation occurs it can be handled by those familiar with the art. Although recycling of the entire raffinate to the distillation is preferred, it is to be understood that all or a portion of the raffinate may not be recycled to the column, but treated in a known manner for recovering the phenol values it contains (e.g. by distillation, etc.).

The organic liquid phase (extract) which contains the extraction solvent, MBF and other impurities, and some phenol, after separation from the water-phenol mixture, may then be treated with a base, such as sodium hydroxide to recover any phenol present therein in an aqueous phase in which the phenol is dissolved as a phenate. Such water soluble phenate may then be subjected to a "springing" operation, as known in the art, in order to recover the phenol.

The remaining organic solvent, which contains MBF and other impurities, may then be further treated to recover organic solvent for recycle to the extraction. Thus, for example, the organic solvent may be recovered free or essentially free of MBF and other impurities by subjecting the solvent to a distillation operation.

The extraction of the MBF and the other impurities from the homogeneous single phase liquid mixture of phenol and water may be accomplished by any one of wide variety of extraction procedures, including staging, recycling part of the extract or raffinate and the like. The selection of an optimum procedure is deemed to be within the scope of those skilled in the art from the teachings herein.

The crude phenol, which is subjected to distillation in the presence of water, is generally a crude phenol which has been initially treated with a base and optionally an acid or acid anhydride as hereinabove described. Such crude phenol generally contains about 50 to 150 ppm of MBF and may further contain other impurities such as mesityl oxide, acetophenone, acetone, cumene, AMS, and some unknowns. By proceeding in accordance with the present invention, it is possible to recover from the distillation a phenol product (generally recovered as a bottoms), which contains less than 30 ppm of MBF, and in most cases, less than 20 ppm of MBF. Furthermore, at least 60% of the phenol present in the overhead, and in most cases, at least 70% and preferably 90% to 95% of the phenol present in said overhead is recovered as raffinate (in the water phase) which raffinate may be recycled to the distillation for ultimate recovery of high purity phenol therefrom.

The distillation of crude phenol, containing MBF, in the presence of water, is generally effected in a suitable tower which, when operated at approximate atmospheric pressure will have an overhead temperature of 95° to 105° C., and a bottoms temperature of from 180° to 190° C. The operating pressure can be atmospheric, or either higher or lower than atmospheric without departing from the teachings of this invention. As should be understood, the overhead and bottoms temperatures will vary with the pressure employed.

The composition of the product recovered at the top of the tower corresponds, or is close, to that of the azeotropic mixture at the operating pressure.

Although the preferred feed is a phenol produced through the cumene route which has been treated with a base, and an acid or acid anhydride, it is to be understood that the present invention is not limited to such a feed.

The invention will be further described with respect to the accompanying drawing, wherein:

The drawing is a simplified schematic flow diagram of a preferred embodiment of the invention.

Referring now to the drawing, a crude phenol, in line 10, which includes MBF and other impurities such as one or more of acetone, alpha-methylstyrene, cumene, acetol, mesityl oxide, and acetophenone, is introduced into a top portion of a steam distillation column generally designated as 11. Steam to supply energy for the distillation is introduced into the bottom and side reboilers of the column. Other heat sources (such as hot oil, other hot process streams, etc.) may be used. A recycle stream containing phenol and water, obtained as hereinafter described, is introduced into the top portion of the column through line 14. Make-up water (not shown) may be provided to the column as liquid or vapor.

The column is operated at a temperature and pressure to separate the impurities from the phenol. Such conditions are as hereinabove described, with a water-phenol azeotrope, which includes the impurities, such as MBF, acetone and the like, being recovered from the top of the column through line 15. Phenol, essentially free of these impurities, and containing less than 30 ppm, preferably less than 20 ppm of MBF, is recovered from the bottom of column 11 through line 16 for introduction into a further column for recovery of high purity phenol product.

The overhead in line 15 is condensed and introduced into an extraction zone, schematically generally indicated as 21 to extract MBF therefrom.

The extraction zone 21 is provided with extraction solvent, such as cumene through line 22. As apparent to those familiar to the art, such as extraction can be effected in many ways for example, it can be a single-staged or a multistaged unit.

The extraction zone 21 is operated at a temperature as hereinabove described in order to maintain the phenol-water mixture as a single liquid phase. Moreover, the extraction solvent is provided in a minimum amount so as to extract MBF and other impurities, without extracting excessive amount of phenol into the organic solvent.

A phenol-water mixture containing a reduced amount of impurities is recovered from extraction zone 21 for recycle to column 11 through line 14.

An organic extraction phase is recovered from extraction zone 21 through line 24, and such organic phase, includes in addition to the extraction solvent, some phenol, MBF, and other impurities. The organic phase in line 24 is then introduced into zone 25 wherein the organic phase is contacted with aqueous base, such as sodium hydroxide, introduced through line 26 for the purpose of converting any phenol to sodium phenate, which is water soluble, while MBF and other impurities are not, and they remain in the organic solvent. Such recovery of phenol from an organic phase is well-known in the art, and no further details are required for a complete understanding of the present invention. Aqueous sodium phenate is recovered from zone 25 through line 30 for subsequent treatment to recover phenol. The recovery of cumene from the remaining organic phase in line 27 can be effected by the application of standard chemical engineering principals. One such recovery scheme is shown in the drawing. The organic phase in line 27 is introduced into a topping unit, schematically generally indicated as 28 to recover components lighter than cumene as overhead through line 29. The material in line 29 may then be further treated; e.g., by incineration.

The bottoms stream, in line 31 is then introduced into a tailing column 32, designed and operated to recover the organic cumene solvent, as overhead through line 33, and MBF and other heavier components as bottoms through line 34. The cumene in line 33 may be combined with fresh feed cumene in line 35 and the combined stream introduced into extraction zone 21 through line 22.

Although the invention has been described with respect to a preferred embodiment in the accompanying drawing, it is to be understood that the scope of the invention is not to be limited to such embodiment. Moreover, such embodiment may be modified within the spirit and scope of the present invention.

The invention will be further described with respect to the following examples; however, the scope of the invention is not be limited thereby:

EXAMPLE 1

Steam Stripping

Phenol, treated chemically as in U.S. Pat. No. 4,298,756 (hexamethylenediamine followed by phthalic anhydride) was used as feed in the steam distillation of crude phenol. Distillation was carried out in a one-inch ID Oldershaw column having 52 trays. The treated phenol and water (2/1 weight ratio) were fed to the 50th tray. The phenol depleted of MBF was removed continuously from the reboiler, while the azeotropic overhead was removed using a condenser above the 52nd tray. By maintaining the overhead product at 67° C.–70° C., it formed one homogeneous liquid phase.

Table 1 is a summary of the results obtained. Analyses were preformed by gas chromatography.

TABLE 1

| Sample Description | Weight of Sample (g) | Total Impurities in PPM | MBF in PPM |
|---|---|---|---|
| Feed | 1048 g Phenol + 527 g H$_2$O | 516* | 95* |
| Bottom Product | 941 | 133 | 17 |
| Overhead | 578 | 696 | 163 |

*These concentrations refer to the phenol in the feed.

EXAMPLE 2

Extraction

One thousand grams of azeotropic overhead product obtained as in Example 1 were charged to an agitated flask maintained at 75° C., followed by 10 grams of cumene. The mixture was agitated for a short period of time. Agitation was stopped and the milky mixture was allowed to separate at the same temperature. Two liquid phases were separated. The organic phase (Org. #2.1) was 16.3 g. The aqueous phase was then allowed to cool to room temperature upon which a second organic phase was separated and was removed (Org. #2.2=23.3 grams). The feed, organic phases and the aqueous phase were analyzed by gas chromatography. Results are summarized in Table 2.

TABLE 2

| Sample Description | Sample Weight | Total Impurities PPM | MBF PPM | Phenol wt. % | Cumene wt. % |
|---|---|---|---|---|---|
| Feed | 1010 g | 396* | 98.7* | 10.35* | 1.00 |
| Org. #2.1 | 16.3 | 14960 | 4750 | 58.08 | 33.90 |
| Org. #2.2 | 23.3 | 3440 | 674 | 71.11 | 3.73 |
| Aqueous | 970 | 77 | 3 | 7.91 | — |

*These values refer to the homogeneous liquid, prior to the addition of cumene.

EXAMPLE 3

Caustic/Acid Treatment

Four grams of Org. #2.1 obtained as in example 2 were shaken in a separatory funnel with a 5% aqueous solution of NaOH at room temperature. Two phases were separated, an organic phase (Org. #3.1=1.25 g) and an aqueous phase. The aqueous phase was then neutralized with a 10% sulfuric acid solution. A second organic phase was separated (Org. #3.2=0.87 g), and the final aqueous phase was 28.2 grams.

TABLE 3

| Sample Description | Total Impurities | MBF | Phenol | Cumene |
|---|---|---|---|---|
| Feed (Org. #2.1) | 1.052 | 0.475 | 58.08 | 33.90 |
| Org. #3.1 | 2.295 | 1.390 | 0.73 | 76.72 |
| Org. #3.2 | 0.281 | 0.040 | 70.43 | 2.07 |
| Aqueous | 0.006 | 0.000 | 4.71 | — |

NOTE:
All concentrations are in wt. % Balance to 100% is water.

EXAMPLE 4

The following illustrates typical flow stream portions in a process according to the invention, by reference to the embodiment of the drawing. The values are given in kilograms per hour.

TABLE 4

| COMPONENT | STREAM NUMBER | | | | | | |
| | 10 | 14 | 15 | 16 | 22 | 24 | 34 |
|---|---|---|---|---|---|---|---|
| Phenol | 12,500 | 590 | 625 | 12,465 | — | 35 | — |
| MBF | 1.25 | 0.15 | 1.15 | 0.25 | — | 1.0 | — |
| Acetone | 1.25 | 7.50 | 8.75 | — | — | 1.25 | — |
| AMS and Cumene | 1.25 | — | 1.00 | 0.25 | — | 33.0 | — |
| Acetol | 1.25 | — | 1.25 | — | — | 1.25 | — |
| Acetophenone | 1.25 | — | — | 1.25 | — | — | — |
| Water | — | 6250 | 6250 | — | — | — | — |
| Cumene | — | — | — | — | 33 | — | 3.5 |
| Unknown | 1.25 | — | 1.25 | — | — | 1.25 | — |

The present invention is particularly advantageous in that MBF and other impurities may be removed from the water-phenol overhead while maximizing recovery of phenol from said overhead in the water phase for recycle to the column. Accordingly, recycle of phenol to the column can be maximized.

Although Applicants do not intend to be limited to any theoretical reasoning, it is believed that the MBF present in the overhead is preferentially present in the phenol, whereby, in order to maximize the recovery of phenol, while effectively removing MBF and other impurities, the MBF is extracted from a single phase liquid mixture of water and phenol while utilizing minimum amounts of extraction solvent.

Numerous modifications and variations of the present invention are possible in light of the above teachings and, therefore, within the scope of the appended claims, the invention may be practiced otherwise than as particularly described.

What is claimed is:

1. A process for purifying phenol comprising:
   distilling in the presence of water a crude phenol containing impurities comprising methylbenzofuran to recover as separate streams a mixture of phenol and water, containing said impurities, and phenol having a reduced quantity of impurities;
   contacting the recovered mixture with a water immiscible extraction solvent to extract impurities from said mixture, said contacting being effected at a temperature at which the water and phenol in the mixture are completely miscible to provide said water-phenol mixture (is) as a single-phase liquid, said extraction solvent being employed in an amount whereby at least 60% of the phenol of the recovered mixture is contained in a remaining mixture of water and phenol; and separating the solvent containing extracted impurities from the remaining mixture of water and phenol, said remaining mixture containing at least 60% of the phenol in the recovered mixture subjected to said contacting.

2. The process of claim 1 wherein at least a portion of the remaining mixture of phenol and water is recycled to the distilling.

3. The process of claim 2 wherein the extraction solvent is employed in an amount no greater than 5 volume percent of the recovered mixture.

4. The process of claim 3 wherein the extraction solvent is employed in an amount no greater than 1 volume percent of the recovered mixture.

5. The process of claim 3 wherein the contacting is effected at a temperature of at least 67° C.

6. The process of claim 5 wherein the extraction solvent is selected from the group consisting of aromatic hydrocarbons, aliphatic hydrocarbons and chlorinated hydrocarbons.

7. The process of claim 6 wherein at least 70% of the phenol in the recovered mixture subjected to said contacting is present in said remaining mixture.

8. The process of claim 7 wherein the extraction solvent is cumene.

9. The process of claim 2 wherein the phenol-water mixture is recovered from the distilling as an overhead azeotrope.

10. The process of claim 2 wherein the phenol recovered from the distilling contains less than 30 ppm of methylbenzofuran.

11. The process of claim 1 wherein the extraction solvent is employed in an amount of from 0.1 to 1 volume percent of the recovered mixture.

* * * * *